(12) United States Patent
Schumacher et al.

(10) Patent No.: US 7,686,881 B2
(45) Date of Patent: Mar. 30, 2010

(54) FLAME-HYDROLYTICALLY PRODUCED TITANIUM DIOXIDE POWDER

(75) Inventors: Kai Schumacher, Hofheim (DE); Andreas Schild, Grenzach-Wyhlen (DE); Martin Moerters, Rheinfelden (DE)

(73) Assignee: Degussa AG, Duesseldorf (DE)

( * ) Notice: Subject to any disclaimer, the term of this patent is extended or adjusted under 35 U.S.C. 154(b) by 388 days.

(21) Appl. No.: 10/580,325

(22) PCT Filed: Nov. 24, 2004

(86) PCT No.: PCT/EP2004/013317
§ 371 (c)(1),
(2), (4) Date: May 24, 2006

(87) PCT Pub. No.: WO2005/054136
PCT Pub. Date: Jun. 16, 2005

(65) Prior Publication Data
US 2007/0144076 A1    Jun. 28, 2007

(30) Foreign Application Priority Data
Dec. 3, 2003  (DE) .......................... 103 57 508
Nov. 16, 2004 (DE) .......................... 10 2004 055 165

(51) Int. Cl.
| | |
|---|---|
| A61K 8/00 | (2006.01) |
| A61K 8/18 | (2006.01) |
| A61K 9/14 | (2006.01) |
| A61Q 17/04 | (2006.01) |
| C09K 3/14 | (2006.01) |
| B24D 3/02 | (2006.01) |
| C09C 1/68 | (2006.01) |
| B01J 23/00 | (2006.01) |
| C01G 23/047 | (2006.01) |
| C09D 1/00 | (2006.01) |
| C23C 16/40 | (2006.01) |
| C04B 14/00 | (2006.01) |
| C09C 1/04 | (2006.01) |
| C09C 1/36 | (2006.01) |

(52) U.S. Cl. .................. 106/430; 106/436; 106/437; 106/286.4; 106/287.19; 502/350; 423/610; 423/611; 423/612; 423/613; 51/309; 424/59; 424/489

(58) Field of Classification Search ............... 502/350; 423/610–613; 106/430, 436, 437, 286.4, 106/287.19
See application file for complete search history.

(56) References Cited

U.S. PATENT DOCUMENTS 4,048,290 A * 9/1977 Lee ........................... 423/336

(Continued)

FOREIGN PATENT DOCUMENTS

EP    0 802 158    10/1997

(Continued)

OTHER PUBLICATIONS

U.S. Appl. No. 11/572,018, filed Jan. 12, 2007, Lortz, et al.

Primary Examiner—Patricia L Hailey
(74) Attorney, Agent, or Firm—Oblon, Spivak, McClelland, Maier & Neustadt, L.L.P.

(57) ABSTRACT

Flame-hydrolytically produced titanium dioxide powder that is present in the form of aggregates of primary particles, and has a BET surface of 20 to 200 $m^2/g$, a half width (HW) [nm] of the primary particle distribution of HW = a×BET$^f$ where a = 670×10$^{-9}$ $m^3/g$ and $-1.3 \le f \le -1.0$ and the proportion of particles with a diameter of more than 45 μm lies in a range from 0.0001 to 0.05 wt. %. The powder is produced by a process in which a titanium halide is vapourised at temperatures of less than 200°C., the vapours are transferred to a mixing chamber by means of a carrier gas of defined moisture content and, separately from this, hydrogen, primary air, which may optionally be enriched with oxygen and/or preheated, and steam are added to the mixing chamber, following which the reaction mixture is combusted in a reaction chamber sealed from the ambient air, secondary air is in addition introduced into the reaction chamber, the solid is then separated from gaseous substances, and following this the solid is treated with steam. The titanium dioxide powder may be used for the heat stabilisation of polymers.

19 Claims, 1 Drawing Sheet

U.S. PATENT DOCUMENTS

| | | | |
|---|---|---|---|
| 5,061,473 A * | 10/1991 | De Cleyn et al. | 423/610 |
| 5,697,177 A * | 12/1997 | Ludlow et al. | 40/665 |
| 6,328,944 B1 | 12/2001 | Mangold et al. | |
| 6,479,031 B2 * | 11/2002 | Ohmori et al. | 423/610 |
| 7,217,407 B2 * | 5/2007 | Zhang | 423/610 |
| 2002/0004029 A1 | 1/2002 | Jang et al. | |
| 2002/0018741 A1 * | 2/2002 | Hemme et al. | 423/210 |
| 2004/0161380 A1 * | 8/2004 | Zimehl et al. | 423/610 |
| 2006/0159636 A1 * | 7/2006 | Meyer et al. | 424/59 |
| 2008/0098932 A1 * | 5/2008 | Perlet et al. | 106/287.19 |

FOREIGN PATENT DOCUMENTS

| | | |
|---|---|---|
| JP | 2001151510 | 6/2001 |
| JP | 2004-331427 | * 11/2004 |
| WO | 96/06803 | 3/1996 |
| WO | 2004/056927 | 7/2004 |

* cited by examiner

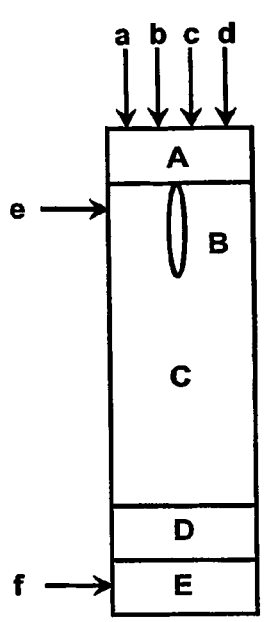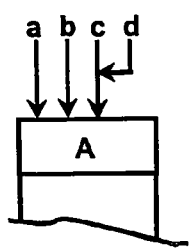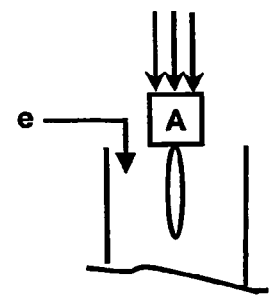
Fig. 1A        Fig. 1B        Fig. 1C
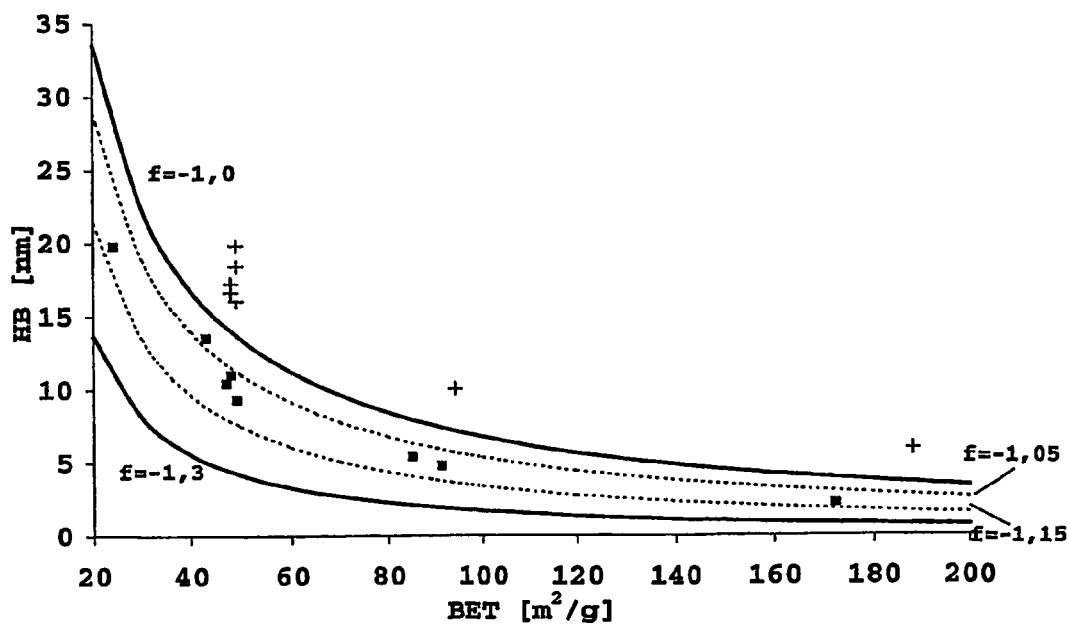
Fig. 2

FLAME-HYDROLYTICALLY PRODUCED TITANIUM DIOXIDE POWDER

The invention relates to flame-hydrolytically produced titanium dioxide powder, and its production and use.

It is known that titanium dioxide can be produced by pyrogenic processes. Pyrogenic processes are understood to include flame oxidations or flame hydrolyses. In flame oxidation a titanium dioxide precursor, for example titanium tetrachloride, is oxidised with oxygen according to equation 1a. In flame hydrolysis the formation of titanium dioxide is effected by hydrolysis of the titanium dioxide precursor, the water necessary for the hydrolysis being derived from the combustion of a fuel gas, for example hydrogen, and oxygen (equation 1b).

(equation 1a)

(equation 1b)

EP-A-1231186 claims a titanium dioxide with a BET surface of between 3 and 200 m²/g with a weight-related $D_{90}$ diameter of the particles of 2.2 μm or less. $D_{90}$ diameters of between 0.8 and 2.1 μm are mentioned in the examples of implementation. In addition, a titanium dioxide is obtained with a BET surface of between 3 and 200 m²/g and a distribution constant n of 1.7 or more, calculated according to the formula R=100 exp(-bD$^n$), where D denotes the particle diameter and b is a constant. The value n is obtained from the three values $D_{10}$, $D_{50}$ and $D_{90}$, which are related to one another by an approximate straight line. The titanium dioxide is obtained by a flame oxidation of titanium tetrachloride and an oxidising gas, the starting materials being pre-heated to a temperature of at least 500° C. before the reaction. In preferred embodiments the velocity of the reaction mixture is 10 m/sec or more, and the residence time in the reaction space is 3 sec or less.

In EP-A-778812 a process for the production of titanium dioxide by a combination of flame oxidation and flame hydrolysis is described. In this connection titanium tetrachloride in the vapour state and oxygen are mixed in a reaction zone and the mixture is heated in a flame that is generated by combustion of a hydrocarbon as fuel gas. The titanium tetrachloride is fed into the central core of the reactor, the oxygen is fed into a tubular sleeve surrounding the central core, and the fuel gas is fed into a tubular sleeve that surrounds those tubes that convey the titanium tetrachloride and oxygen.

A laminar diffusion flame reactor is preferably employed. In this method it is possible to produce highly surface-active titanium dioxide powder containing a large proportion of the anatase modification. In EP-A-778812 no information is given regarding the structure and size of the primary particles and aggregates. However, it is these quantities in particular that are important for many applications, for example in cosmetics applications or as an abrasive in dispersions for the electronics industry. The mechanism of the formation of the titanium dioxide according to EP-A-778812 includes both a flame oxidation (equation 1a) as well as a flame hydrolysis (equation 1b). Although the different formation mechanisms enable the anatase fraction to be controlled, a specific distribution of the primary particles and aggregates cannot however be achieved. A further disadvantage of this method, as is mentioned in US-A-20002/0004029, is the incomplete conversion of titanium tetrachloride and fuel gas and the resultant grey colouration of the titanium dioxide.

These problems are eliminated according to US-A-20002/0004029, by now using five tubes instead of the three tubes as described in EP-A-778812. For this, titanium tetrachloride vapour, argon, oxygen, hydrogen and air are simultaneously metered into a flame reactor. The disadvantage of this method is the use of the expensive noble gas argon and a low yield of titanium dioxide due to low concentrations of titanium tetrachloride in the reaction gas.

A titanium dioxide powder produced by flame hydrolysis has for a long time been marketed by Degussa under the reference P 25.

This is a finely particulate titanium dioxide powder with a specific surface of 50±15 m²/g, a mean size of the primary particles of 21 nm, a compacted bulk density (approximate value) of 130 g/l, an HCl content of less than or equal to 0.300 wt. % and a screening residue according to Mocker (45 μm) of less than or equal to 0.050%. This powder has good properties for many applications.

The prior art demonstrates the wide interest in pyrogenically produced titanium dioxide. In this connection it is found that the common generic term "pyrogenic", i.e. flame hydrolysis and flame oxidation, is not an adequate description of titanium dioxide. On account of the complexity of the pyrogenic processes only a few substance parameters can be specifically adjusted.

Titanium dioxide is employed in particular in catalysis, for example photocatalysis, in cosmetics, for example sunscreen agents, as an abrasive in the form of dispersions in the electronics industry, or for heat stabilisation of polymers. In these uses increasing demands are placed on the purity and structure of the titanium dioxide. Thus, it is for example important that, when using titanium dioxide as an abrasive in dispersions, the titanium dioxide has a good dispersibility and is as far as possible free from coarse particles that can scratch the surface to be polished.

The object of the present invention is to provide a titanium dioxide powder that has a high purity, is easy to disperse, and is as far as possible free of coarse fractions.

The object of the present invention is also to provide a process for the production of the titanium dioxide powder. In this connection the process should be able to be implemented on an industrial scale.

The present invention provides a flame-hydrolytically produced titanium dioxide powder that is present in aggregates of primary particles, characterised in that it has a BET surface of 20 to 200 m²/g and the half width HW, in nanometers, of the primary particle distribution has values between HW [nm]=a×BET$^f$ where a=670×10$^{-9}$ m³/g and −1.3≦f≦−1.0 and the proportion of particles with a diameter of more than 45 μm is in a range from 0.0001 to 0.05 wt. %.

The term primary particles in the context of the invention is understood to denote particles that are first of all formed in the reaction and that can coalesce to form aggregates during the further course of the reaction.

The term aggregate within the context of the invention is understood to denote primary particles of similar structure and size that have coalesced together, and whose surface is smaller than the sum of the individual, isolated primary particles. Several aggregates or also individual primary particles may combine together further to form agglomerates. Aggregates or primary particles accordingly lie adjacent to one another in the form of point objects. Depending on their degree of coalescence, agglomerates may be broken up by application of energy.

Aggregates on the other hand can be broken up only by a high input of energy or even cannot be broken up at all. Intermediate forms exist.

The mean half width HW of the primary particle distribution (in numerical terms) is obtained by image analysis of the TEM photographs. According to the invention the mean half width is a function of the BET surface with a constant f, where $-1.3 \leq f \leq -1.0$. Preferably the half width may lie in the range $-1.2 \leq f \leq -1.1$.

It is the high BET surface, the narrow distribution of the primary particle distribution and the low proportion of aggregates with a diameter of more than 45 μm, which lies in a range from 0.0001 to 0.05 wt. %, that are relevant for the positive properties of the powder according to the invention, for example when polishing surfaces. No flame-hydrolytically produced titanium dioxide powders are known in the prior art that simultaneously exhibit these features. It is of course possible for example to remove to a large extent powders according to the prior art mechanically from aggregates with a diameter of more than 45 μm, though the resultant powder would however not be able to achieve the ranges claimed by the present invention as regards BET surface and half width values of the primary particles.

The BET surface of the titanium dioxide powder according to the invention lies in a wide range from 20 to 200 $m^2/g$. It has proved advantageous if the BET surface lies in a range from 40 to 60 $m^2/g$. A range of 45 to 55 $m^2/g$ may be particularly advantageous.

For a titanium dioxide powder according to the invention with a BET surface between 40 and 60 $m^2/g$, the 90% spread of the number distribution of the primary particle diameters may lie between 10 and 100 nm. As a rule the 90% spread of the number distribution of the primary particle diameters is between 10 and 40 nm.

Furthermore, the equivalent circular diameter of the aggregates (ECD) of such a titanium dioxide powder may be less than 80 nm.

The mean aggregate area of a titanium dioxide powder according to the invention with a BET surface of 40 to 60 $m^2/g$ may be less than 6500 $nm^2$ and the mean aggregate circumference may be less than 450 nm.

In addition the BET surface of the titanium dioxide powder according to the invention may lie in a range from 80 to 120 $m^2/g$. A range of 85 to 95 $m^2/g$ may be particularly preferred.

For a titanium dioxide powder according to the invention with a BET surface between 80 and 120 $m^2/g$, a 90% spread of the number distribution of the primary particle diameters may have values between 4 and 25 nm. Furthermore, such a titanium dioxide powder may have an equivalent circular diameter of the aggregates (ECD) of less than 70 nm.

The mean aggregate area of a titanium dioxide powder according to the invention with a BET surface of 80 to 120 $m^2/g$ may be less than 6000 $nm^2$ and the mean aggregate circumference may be less than 400 nm.

The proportion of aggregates and/or agglomerates of the titanium dioxide powder according to the invention with a diameter of more than 45 μm lies in a range from 0.0001 to 0.05 wt. %. A range from 0.001 to 0.01 wt. % may be preferred, and a range from 0.002 to 0.005 wt. % may be particularly preferred.

The titanium dioxide powder according to the invention comprises rutile and anatase as crystal modifications. In this connection the anatase/rutile proportion for a given surface may lie in a range from 2:98 to 98:2. The range from 80:20 to 95:5 may be particularly preferred.

The titanium dioxide powder according to the invention may contain residues of chloride. The chloride content is preferably less than 0.1 wt. %. A titanium dioxide powder according to the invention with a chloride content in the range from 0.01 to 0.05 wt. % may be particularly preferred.

The compacted bulk density of the titanium dioxide powder according to the invention is not limited. It has however proved advantageous if the compacted bulk density has values from 20 to 200 g/l. A compacted bulk density of 30 to 120 g/l may be particularly preferred.

The present invention also provides a process for the production of the titanium dioxide powder according to the invention, which is characterised in that a titanium halide, preferably titanium tetrachloride, is vapourised at temperatures of less than 200° C., the vapours are transferred to a mixing chamber by means of a carrier gas with a proportion of steam in a range from 1 to 25 μg/$m^3$, and separately from this, hydrogen, primary air, which may optionally be enriched with oxygen and/or pre-heated, and steam are transferred to the mixing chamber, wherein the proportion of steam is in a range from 1 to 25 g/$m^3$ primary air, the lambda value lies in the range from 1 to 9 and the gamma value lies in the range from 1 to 9, following which the mixture consisting of the titanium halide vapour, hydrogen, air and steam is ignited in a burner and the flame burns back into a reaction chamber sealed from the ambient air, wherein a vacuum of 1 to 200 mbar exists in the reaction chamber, the exit velocity of the reaction mixture from the mixing chamber to the reaction space lies in a range from 10 to 80 m/sec, in addition secondary air is introduced into the reaction chamber, wherein the ratio of primary air to secondary air is between 10 and 0.5, following which the solid is separated from gaseous substances, and the solid is then treated with steam.

An essential feature of the process according to the invention is that the titanium halide is vapourised at temperatures below 200° C. and the vapours are conveyed to the mixing chamber by means of a carrier gas, for example air or oxygen, which has a defined carrier gas moisture content. It has been found for example that the product quality decreases at higher vapourisation temperatures.

Moreover it has also been found that, within the claimed steam content of 1 to 25 g/$m^3$ of gas, or primary air, there is no noticeable hydrolysis of the titanium halide in the form of caking, whereas on the other hand the steam content influences the subsequent primary particle and aggregate structure. Outside the claimed range, no powder according to the invention can be obtained. In a preferred embodiment the steam content is between 5 and 20 g/$m^3$ of gas, or primary air.

As carrier gas, air may also be used. This permits a higher space-time yield in the reaction chamber than when using an inert gas.

Furthermore, the exit velocity of the reaction mixture from the mixing chamber into the reaction space lies in a range from 10 to 0.80 m/sec. In a preferred embodiment the exit velocity is between 15 and 60 m/sec, and in a particularly preferred embodiment is between 20 and 40 m/sec. At values below this a uniform powder is not obtained, but instead a powder is obtained that contains particles of diameter 45 μm or more in an amount of more than 0.05 wt. %.

In addition the reaction must be carried out so that the lambda value lies in the range from 1 to 9 and the gamma value lies in the range from 1 to 9.

Flame-hydrolytically produced oxides are normally obtained so that the gaseous starting substances are in a stoichiometric ratio with respect to one another such that the added hydrogen is at least sufficient to react with the halogen X present from the titanium halide TiX$_4$ to form HX. The amount of hydrogen required for this purpose is termed the stoichiometric amount of hydrogen.

The ratio of the added hydrogen to the stoichiometrically necessary hydrogen defined above is termed gamma. Gamma is defined as:

Gamma=added hydrogen/stoichiometrically required hydrogen or

Gamma=H$_2$ fed in (moles)/H$_2$ stoichiometric (moles).

With flame-hydrolytically produced oxides in addition an amount of oxygen (for example from the air) is normally used that is at least sufficient to convert the titanium halide into titanium dioxide and to convert excess hydrogen that may still be present into water. This amount of oxygen is termed the stoichiometric amount of oxygen.

Similarly, the ratio of added oxygen to stoichiometrically required oxygen is termed lambda, and is defined as follows:

Lambda=added oxygen/stoichiometrically required oxygen or

Lambda=O$_2$ fed in (moles)/O$_2$ stoichiometric (moles).

Moreover, in the process according to the invention, in addition to the primary air in the mixing chamber air (secondary air) is directly introduced into the reaction chamber. It has been found that, without the addition of the additional air into the mixing chamber, no titanium dioxide powder according to the invention is obtained. In this connection it should be noted that the ratio of primary air to secondary air is between 10 and 0.5. The ratio is preferably in a range between 5 and 1.

In order to be able accurately to meter in the amount of secondary air, it is necessary to cause the flame to burn back into a reaction chamber sealed from the ambient air. This enables the process to be accurately controlled, which is essential in order to obtain the titanium dioxide powder according to the invention. The vacuum in the reaction chamber is preferably between 10 and 80 mbar.

An essential feature is also the fact that titanium dioxide powder after separation from gaseous substances should be treated with steam. This treatment is primarily intended to remove halide-containing groups from the surface. At the same time this treatment reduces the number of agglomerates. The process may be carried out continuously in such a way that the powder is treated, in counter-current or co-current, with steam, possibly together with air, in which connection the steam is always introduced from below into an upright, heatable column. The feed of the powder may take place from the top or the bottom of the column. The reaction conditions may be chosen so that a fluidised bed is formed. The temperature at which the treatment with steam is carried out is preferably between 250 and 750° C., values from 450 to 550° C. being preferred. In addition it is preferred to carry out the treatment in counter-current in such a way that a fluidised bed is not formed.

Moreover it may be advantageous to introduce the steam together with the air into the mixing chamber.

BRIEF DESCRIPTION OF THE DRAWINGS

FIG. 1A shows an arrangement for carrying out one embodiment of the invention in an apparatus including a mixing chamber;

FIG. 1B shows a portion of an apparatus used to carry out one embodiment in which steam and air are introduced into a mixing chamber;

FIG. 1C shows an open reaction chamber in which secondary air is aspirated;

FIG. 2 shows how half width and BET properties of the examples correlate with certain ranges.

FIG. 1A shows diagrammatically an arrangement for carrying out the process according to the invention. In the figure: A=mixing chamber, B=flame, C=reaction chamber, D=solid/gaseous separation, E=post-treatment with steam. The substances used are identified as follows: a=mixture of titanium halide and carrier gas with defined moisture content, b=hydrogen, c=air, d=steam, e=secondary air, f=steam or steam/air. FIG. 1B shows a section of the arrangement of FIG. 1A. In this, the steam (d) together with the air (c) are introduced into the mixing chamber. FIG. 1C shows an open reaction chamber in which the secondary air e is aspirated from the surroundings. With the arrangement according to FIG. 1C no titanium dioxide powder according to the invention can be obtained.

The invention also provides for the use of the titanium dioxide powder according to the invention for the heat protection stabilisation of silicones.

The invention in addition provides for the use of the titanium dioxide powder according to the invention in sunscreen agents.

The invention furthermore provides for the use of the titanium dioxide powder according to the invention as a catalyst, as a catalyst carrier, as a photocatalyst, and as an abrasive for the production of dispersions.

EXAMPLES

Analysis

The BET surface is determined according to DIN 66131.

The compacted bulk density is determined on the basis of DIN ISO 787/XI K 5101/18 (not screened).

The bulk density is determined according to DIN-ISO 787/XI.

The pH value is determined on the basis of DIN ISO 787/IX, ASTM D 1280, JIS K 5101/24.

The proportion of particles larger than 45 μm is determined according to DIN ISO 787/XVIII, JIS K 5101/20.

Determination of the chloride content: ca. 0.3 g of the particles according to the invention is accurately weighed out, 20 ml of 20 percent sodium hydroxide solution (analysis purity) are added thereto, dissolved, and transferred while stirring to 15 ml of cooled HNO$_3$. The chloride content in the solution is titrated with AgNO$_3$ solution (0.1 mole/l or 0.01 mole/l).

The half width of the primary particle distribution and area, circumference and diameter of the aggregates are determined by means of image analysis. The image analyses are carried out using an H 7500 TEM instrument from Hitachi and a MegaView II CCD camera from SIS. The image magnification for the evaluation is 30000:1 at a pixel density of 3.2 nm. The number of evaluated particles is greater than 1000. The preparation is carried out according to ASTM3849-89. The lower threshold boundary as regards detection is 50 pixels.

Example A1

According to the Invention 160 kg/hr of TiCl$_4$ are vapourised in an evaporator at 140° C. The vapours are transferred to a mixing chamber by means of nitrogen (15 Nm$^3$/hr) as carrier gas with a carrier gas moisture content of 15 g/m$^3$ of carrier gas. Separately from this, 52 Nm$^3$/hr of hydrogen and 525 Nm$^3$/hr of primary air are introduced into the mixing chamber. In a central tube the reaction mixture is fed to a burner and ignited. The flame burns in a water-cooled flame tube. In addition 200 Nm$^3$/hr of secondary air are added to the reaction space. The powder formed is separated in a downstream filter and then treated in countercurrent with air and steam at 520° C.

The Examples A2 to A9 according to the invention are carried out similarly to A1. The parameters altered in each case are listed in Table 1.

The physicochemical data of the powders from Examples A1 to A9 are shown in Table 2.

The comparison examples B1 to B3 and B5 to B8 are also carried out similarly to A1. The parameters altered in each case are listed in Table 1.

The comparison example B4 is carried out using an open burner. The amount of secondary air is not determined.

The physicochemical data of the powders from Examples B1 to B8 are shown in Table 2.

Table 3 shows the calculated half width of the primary particles depending on the BET surface area with f=−1.0, −1.05, −1.15 und −1.3. The factor $10^{-9}$ is the basis for the conversion of meter into nanometer. As factor f can only be negative, the unit of BET$^f$ is g/m2.

FIG. 2 shows the half width of the primary particles of the titanium dioxide powders produced in the examples. In this connection the titanium dioxide powders according to the invention (identified as ■) lie within the claimed half width HW [nm]=a×BET$^f$ where a=670×10$^{-9}$ m$^3$/g and −1.3≦f≦−1.0, while the comparison examples (identified by +) lie outside.

TABLE 1

Process parameters in the production of the titanium dioxide powders

| Ex. | TiCl$_4$ kg/h | T$_V$ | Carrier Gas Nm$^3$/h | Carrier Gas Moisture g/m$^3$ | H$_2$ Nm$^3$/h | Primary Air Nm$^3$/h | Primary Air Moisture g/m$^3$ | Secondary Air Nm$^3$/h | Gamma | Lambda | v m/s | T$_E$ ° C. |
|---|---|---|---|---|---|---|---|---|---|---|---|---|
| A1 | 160 | 140 | 15 | 15 | 52 | 525 | 15 | 200 | 1.38 | 3.55 | 27 | 520 |
| A2 | 160 | 140 | 15 | 15 | 52 | 525 | 10 | 200 | 1.38 | 3.55 | 27 | 650 |
| A3 | 160 | 140 | 3 | 10 | 52 | 635 | 15 | 200 | 1.38 | 5.15 | 31 | 450 |
| A4 | 160 | 140 | 15 | 10 | 82 | 415 | 15 | 200 | 2.17 | 2.25 | 23 | 520 |
| A5 | 200 | 140 | 40 | 8 | 52 | 500 | 10 | 200 | 1.1 | 4.3 | 26 | 520 |
| A6 | 40 | 140 | 15 | 15 | 67 | 535 | 10 | 200 | 7.08 | 3.44 | 27 | 520 |
| A7 | 40 | 140 | 15 | 6 | 67 | 550 | 10 | 200 | 7.08 | 3.54 | 27 | 520 |
| A8 | 40 | 140 | 15 | 22 | 60 | 780 | 10 | 200 | 6.34 | 5.55 | 38 | 520 |
| A9 | 160 | 140 | 15 | 2 | 52 | 225 | 10 | 200 | 1.38 | 1.93 | 14 | 520 |
| B1 | 160 | 250 | 15 | 10 | 52 | 525 | 10 | 200 | 1.38 | 3.55 | 27 | 520 |
| B2 | 160 | 140 | 15 | 40 | 52 | 525 | 10 | 200 | 1.38 | 3.55 | 27 | 520 |
| B3 | 160 | 140 | 15 | 10 | 52 | 1200 | 12 | 200 | 1.37 | 9.67 | 56 | 520 |
| B4 | 160 | 140 | 15 | 10 | 52 | 525 | 12 | ** | 1.38 | 3.55 | 27 | 520 |
| B5 | 40 | 140 | 15 | 10 | 70 | 560 | 12 | 10 | 7.4 | 3.35 | 26 | 650 |
| B6 | 160 | 140 | 15 | 10 | 52 | 525 | 12 | 200 | 1.38 | 3.55 | 27 | — |
| B7 | 160 | 140 | 15 | 10 | 52 | 525 | 15 | 0 | 1.38 | 3.55 | 27 | 520 |
| B8 | 160 | 220 | 15 | 10 | 52 | 525 | 15 | 50 | 1.38 | 3.55 | 27 | 520 |

T$_V$ = temperature of evaporator; T$_E$ = deacidification temperature; B4: = open burner, no secondary air measurement; v = exit velocity of the reaction mixture from the mixing chamber into the reaction space

TABLE 2

Physicochemical parameters of the titanium dioxide powders

| Ex. | BET m2/g | Primary Particles Half Width nm | Aggregates ECD nm | Aggregates Avg. Area nm2 | Aggregates Avg. Circmf. nm | Particles >45 μm % | Anatase % | Bulk Density g/l | Compacted Bulk Density g/l | Chlorine Content Wt. % | pH-Value |
|---|---|---|---|---|---|---|---|---|---|---|---|
| A1 | 48 | 11.0 | 67.4 | 4976 | 366.3 | 0.001 | 89 | 84 | 114 | 0.02 | 3.8 |
| A2 | 47 | 10.4 | 66.4 | 5112 | 369.5 | 0.001 | 89 | 88 | 115 | 0.15 | 4.2 |
| A3 | 49 | 9.3 | 65.3 | 4827 | 371.9 | 0.002 | 85 | 87 | 108 | 0.1 | 3.8 |
| A4 | 24 | 19.8 | n.d. | n.d. | n.d. | 0.003 | 52 | 96 | 114 | 0.05 | 4.0 |
| A5 | 43 | 13.5 | 66.5 | 5140 | 380.75 | 0.002 | 92 | 88 | 110 | 0.11 | 3.8 |
| A6 | 85 | 5.4 | 63.1 | 5017 | 341.0 | 0.010 | 93 | 102 | 122 | 0.15 | 3.9 |
| A7 | 91 | 4.8 | 62.4 | 5314 | 331.5 | 0.008 | 90 | 99 | 125 | 0.13 | 3.8 |
| A8 | 172 | 2.2 | 60.1 | 5128 | 321.0 | 0.009 | 96 | 115 | 158 | 0.09 | 3.7 |
| A9 | 49 | 34.3 | n.d. | n.d. | n.d. | 0.002 | 71 | 112 | 143 | 0.04 | 4.0 |
| B1 | 48 | 17.2 | 75.8 | 6525 | 448.3 | 0.019 | 89 | 83 | 106 | 0.03 | 3.8 |
| B2 | 49 | 16.0 | 81.2 | 6713 | 481.0 | 0.025 | 91 | 84 | 108 | 0.11 | 3.9 |
| B3 | 188 | 5.9 | 77.9 | 6418 | 452.3 | 0.004 | 97 | 111 | 162 | 0.09 | 4.0 |
| B4 | 48 | 16.6 | 82.3 | 7214 | 474.8 | 0.010 | 87 | 89 | 111 | 0.04 | 3.9 |
| B5 | 94 | 10.0 | n.d. | n.d. | n.d. | n.d. | n.d. | n.d. | n.d. | n.d. | n.d. |
| B6 | 51 | n.d. | n.d. | n.d. | n.d. | n.d. | n.d. | n.d. | n.d. | 1.51 | 2.3 |
| B7 | 49 | 18.4 | n.d. | n.d. | n.d. | 0.06 | 85 | n.d. | n.d. | 0.08 | 3.9 |
| B8 | 49 | 19.8 | n.d. | n.d. | n.d. | 0.11 | 87 | n.d. | 116 | 0.1 | 4.0 | n.d. = not determined

TABLE 3

Calculated half width of primary particles

| BET [m2/g] | Half width of primary particles [nm] | | | |
|---|---|---|---|---|
| | $670*10^{-9}*$ $BET^{-1.00}$ | $670*10^{-9}*$ $BET^{-1.05}$ | $670*10^{-9}*$ $BET^{-1.15}$ | $670*10^{-9}*$ $BET^{-1.3}$ |
| 20 | 33.50 | 28.84 | 21.37 | 13.64 |
| 30 | 22.33 | 18.84 | 13.41 | 8.05 |
| 40 | 16.75 | 13.93 | 9.63 | 5.54 |
| 50 | 13.40 | 11.02 | 7.45 | 4.14 |
| 60 | 11.17 | 9.10 | 6.04 | 3.27 |
| 70 | 9.57 | 7.74 | 5.06 | 2.68 |
| 80 | 8.38 | 6.73 | 4.34 | 2.25 |
| 90 | 7.44 | 5.94 | 3.79 | 1.93 |
| 100 | 6.70 | 5.32 | 3.36 | 1.68 |
| 120 | 5.58 | 4.39 | 2.72 | 1.33 |
| 150 | 4.47 | 3.48 | 2.11 | 0.99 |
| 170 | 3.94 | 3.05 | 1.82 | 0.84 |
| 200 | 3.35 | 2.57 | 1.51 | 0.68 |

Heat Stabilisation of Polymers

Example C1

Without Titanium Dioxide Powder (Comparison Example)

A two-component silicone rubber from Bayer, trade name Silopren® LSR 2040, is used as base component (addition crosslinking). After homogeneously mixing the two components with a dissolver the vulcanisation takes place at 180° C. for 10 minutes. Sample plates (ca. 10×15 cm) 6 mm thick are produced. The sample plates are heated at 80° C. in a furnace to constant weight (ca. 1 day). To check the thermal stability to heat a hot storage test is carried out. For this, a sample strip of size 5×7 cm is kept in a circulating air oven at 275° C. The weight loss is measured.

Example C2

Addition of Titanium Dioxide Powder According to the Prior Art (Comparison Example)

A two-component silicone rubber from Bayer, trade name Silopren® LSR 2040, is used as base component (addition crosslinking). 1.5 wt. %, referred to the total batch, of titanium dioxide powder P 25 S (Degussa AG) is incorporated for 5 minutes into one of the components, using a dissolver. Following this the vulcanisation and production of the sample plates take place as described in Example 1.

Sample strips of size 5×7 cm are stored at 275° C. The weight loss is measured.

The Examples C3-5 are carried out similarly to C1, but using the titanium dioxide powders A1 according to the invention in C3, A3 in C4 and A7 in C5, instead of P25 S.

Table 4 shows the changes in length of the samples stored at 275° C. after 1, 3 and 7 days.

The results demonstrate the effective heat protection stabilisation of polymers achieved by using the titanium dioxide powder according to the invention.

TABLE 4

Two-component silicone rubber

| Example | Length Change [%] after | | |
|---|---|---|---|
| | 1 Day | 3 Days | 7 Days |
| C1 (comp.) | 98.6 | — | — |
| C2 (comp.) | 46.3 | 58.9 | 70.0 |
| C3 | 16.3 | 27.9 | 39.5 |
| C4 | 18.7 | 41.8 | 52.7 |
| C5 | 29.0 | 49.0 | 58.0 |

Photocatalytic Activity

Example D1

Titanium Dioxide Powder According to the Prior Art (Comparison Example)

To determine the photocatalytic activity the sample to be measured is suspended in 2-propanol and irradiated for one hour with UV light. The concentration of acetone formed is then measured.

Ca. 250 mg (accuracy 0.1 mg) of titanium dioxide powder P 25S (Degussa AG) are suspended using an Ultra-Turrax stirrer in 350 ml (275.1 g) of 2-propanol. This suspension is conveyed by means of a pump through a cooler thermostatically controlled to 24° C. to a glass photoreactor equipped with a radiation source and flushed beforehand with oxygen. An Hg medium-pressure immersion lamp of the type TQ718 (Heraeus) with an output of 500 Watts serves for example as radiation source. A protective tube of borosilicate glass restricts the emitted radiation to wavelengths >300 nm. The radiation source is surrounded externally by a cooling tube through which water flows. Oxygen is metered into the reactor via a flow meter. The reaction is started when the radiation source is switched on. At the end of the reaction a small amount of the suspension is immediately removed, filtered, and analysed by gas chromatography.

A photoactivity k of $0.68 \times 10^{-3}$ mole $kg^{-1}min^{-1}$ is measured. This is taken as base value 1. The titanium dioxide powder according to the invention has a somewhat lower photocatalytic activity of 0.8 to 0.9.

The invention claimed is:

1. A flame-hydrolytically produced titanium dioxide powder present in aggregates of primary particles, wherein
   the titanium dioxide powder has a BET surface of 40 to 60 $m^2/g$ and
   the half width HW, in nanometers, of the primary particle distribution has values between
   HW (nm)=a×$BET^f$ where a=670×$10^{-9}$ $m^3/g$ and
   $-1.3 \leq f \leq -1.0$
   the proportion of aggregates with a diameter of more than 45 μm is in a range from 0.0001 to 0.05 wt. %, and
   wherein the titanium oxide powder has an
   anatase/rutile ratio of 2:98 to 98:2.

2. The flame-hydrolytically produced titanium dioxide powder according to claim 1, wherein the 90% spread of the number distribution of the primary particle diameters lies in a range from 5 to 100 nm.

3. The flame-hydrolytically produced titanium dioxide powder according to claim 1, wherein the equivalent circular diameter of the aggregates (ECD) is less than 80 nm.

4. The flame-hydrolytically produced titanium dioxide powder according to claim 1, wherein the mean aggregate area is less than 6500 nm².

5. The flame-hydrolytically produced titanium dioxide powder according to claim 1, wherein the mean aggregate circumference is less than 450 nm.

6. The flame-hydrolytically produced titanium dioxide powder according to claim 1, wherein the 90% spread of the number distribution of the primary particles diameters has values from 4 to 25 nm.

7. The flame-hydrolytically produced titanium dioxide powder according to claim 1, wherein the equivalent circular diameter of the aggregates (ECD) is less than 70 nm.

8. The flame-hydrolytically produced titanium dioxide powder according to claim 1, wherein the mean aggregate area is less than 6000 nm².

9. The flame-hydrolytically produced titanium dioxide powder according to claim 1, wherein the mean aggregate circumference is less than 400 nm.

10. The flame-hydrolytically produced titanium dioxide powder according to claim 1, wherein the proportion of aggregates and/or agglomerates with a diameter of more than 45 μm lies in a range from 0.001 to 0.01 wt. %.

11. The flame-hydrolytically produced titanium dioxide powder according to claim 1, wherein it has a chloride content of less than 0.1 wt. %.

12. The flame-hydrolytically produced titanium dioxide powder according to claim 1, wherein the compacted bulk density has values of 20 to 200 g/l.

13. A process for the production of the flame-hydrolytically produced titanium dioxide powder according to claim 1, wherein
a titanium halide is vapourised at temperatures of less than 200° C., the vapours are transferred to a mixing chamber by means of a carrier gas with a proportion of steam in a range from 1 to 25 g/m³, and
separately from this, hydrogen, primary air, which may optionally be enriched with oxygen and/or pre-heated, and steam are transferred to the mixing chamber,
wherein the proportion of steam is in a range from 1 to 25 g/m³ primary air,
the lambda value lies in the range from 1 to 9 and the gamma value lies in the range from 1 to 9,
following which
the mixture consisting of the titanium halide vapour, hydrogen, air and steam is ignited in a burner and the flame burns back into a reaction chamber sealed from the ambient air, wherein
a vacuum of 1 to 200 mbar exists in the reaction chamber,
the exit velocity of the reaction mixture from the mixing chamber to the reaction space lies in a range from 10 to 80 m/sec,
in addition secondary air is introduced into the reaction chamber, wherein
the ratio of primary air to secondary air is between 10 and 0.5,
following which the solid is separated from the gaseous substances, and
the solid is then treated with steam.

14. The process according to claim 13, wherein the steam is introduced together with the air into the mixing chamber.

15. A process according to claim 13, wherein the titanium halide is titanium tetrachloride.

16. A flame-hydrolytically produced titanium dioxide powder according to claim 1 for the heat protection stabilisation of silicones.

17. Sunscreen agents comprising a flame-hydrolytically produced titanium dioxide powder according to claim 1.

18. A catalyst, a catalyst carrier, a photocatalyst, and an abrasive for the production of dispersions comprising a flame-hydrolytically produced titanium dioxide powder according to claim 1.

19. The flame-hydrolytically produced titanium dioxide powder according to claim 1, wherein the BET surface is in a range from 40 to 49 m²/g.

* * * * *